United States Patent [19]

Barker et al.

[11] 4,104,403

[45] Aug. 1, 1978

[54] WATER-OIL EMULSIONS AND METHOD OF PREPARING SAME

[75] Inventors: Graham Barker, Fair Lawn; Martin J. Barabash, Montvale, both of N.J.

[73] Assignee: Witco Chemical Corporation, New York, N.Y.

[21] Appl. No.: 753,147

[22] Filed: Dec. 21, 1976

[51] Int. Cl.² ............... A61K 47/00; A61K 31/00
[52] U.S. Cl. .................. 424/365; 424/61; 424/168; 424/172; 424/DIG. 5
[58] Field of Search .............. 424/365, 61, 168, 172; 425/DIG. 5

[56] References Cited

U.S. PATENT DOCUMENTS

| | | | |
|---|---|---|---|
| 2,447,715 | 8/1948 | Rose | 424/365 |
| 3,081,320 | 3/1963 | Elenbogen | 424/365 |
| 3,149,036 | 9/1964 | Woodhour et al. | 424/365 |
| 3,681,412 | 8/1972 | Betzing | 260/403 |
| 3,875,196 | 4/1975 | Meguro et al. | 260/403 |
| 3,920,819 | 11/1975 | Stephens et al. | 424/365 |
| 3,983,228 | 9/1976 | Woodhour et al. | 424/365 |
| 4,005,190 | 1/1977 | Moder et al. | 424/365 |

FOREIGN PATENT DOCUMENTS

| | | | |
|---|---|---|---|
| 869,799 | 5/1939 | France | 424/365 |
| 854,925 | 11/1960 | United Kingdom | 424/365 |

OTHER PUBLICATIONS

Remington's Pharm. Sci., 15th Ed. (1975), Mack Publishing Co., Easton, Pa., pp. 327–339, 425 and 1257.

*Primary Examiner*—Donald B. Moyer
*Attorney, Agent, or Firm*—Albert L. Gazzola; Morton Friedman

[57] ABSTRACT

Cosmetic emulsions having a high internal phase ratio comprising an oil continuous phase, a water disperse phase, and an emulsifier combination of (i) aluminum and/or calcium stearate and (ii) a phosphated mono- and/or diglyceride; and method of preparing same.

12 Claims, No Drawings

WATER-OIL EMULSIONS AND METHOD OF PREPARING SAME

BACKGROUND

The science of emulsions and the techniques of emulsification are replete with analyses and theories representing continuing efforts to determine the true nature of oil-in-water emulsions (O/W) and water-in-oil emulsions (W/O). The true nature of emulsions involves, inter alia, (i) surface chemistry, e.g., the interfacial tension between the so-called disperse and the continuous phases, (ii) the physical properties of emulsions, including emulsion stability and the tendency to demulsify, to invert, to cream, (iii) the sensitive and very critical function of emulsifying agents, (iv) and the like.

Any number of equations and tables have been derived over the years as researchers persevere in their attempts, for example, to relate the viscosity of an emulsion to the viscosity of its continuous phase, and/or to the concentration of its internal phase, and/or to the interfacial film provided by emulsifying agents, and/or to the type of emulsifier and concentration thereof. Of course, the recondite principles inherent in electrophoretic studies of emulsions dramatically illustrate the quest for insight into the enigmatic entity known as an emulsion.

A well-respected emulsion textbook author, Paul Becher, expresses it better when he admits:

"... emulsion theory has progressed to a point where *some sort of* theoretical interpretation of emulsion behavior is possible; the *prediction* of emulsion behavior is still largely a matter of *art* rather than science." (Emphasis added) [1]

[1] Becher, "Emulsions: Theory and Practice," (1957), page 85, American Chemical Society Monograph Series. Reinhold Publishing Corporation, N.Y.

Typically, while Becher reports that early on it was found that the emulsifying agents "... sodium, potassium and lithium soaps ... give O/W emulsions ... [and] magnesium, strontium, barium, iron and aluminum soaps give W/O emulsions ...,"[2] he is quick to qualify predictability throughout his text when reporting on research findings using mixtures of emulsifying agents, varied concentrations of emulsifying agents, varied internal phase ratios, and the like.

[2] Ibid., page 86; ibid, cf. also page 88.

Another illustration in this vein is the author's discourse on the hydrophilic/lipophilic (polar/non-polar) characteristics of molecules. A linear $C_{12}$ hydrocarbon, for example, terminated at one end with a polar (water-soluble) moiety, such as a carboxy group or its lower alkyl ester, is said to be amphiphilic, i.e., one end of the hydrocarbon is soluble in water and the other end is more soluble in non-polar organic solvents, such as benzene. From these observed characteristics there evolved over the years a method of selecting emulsifiers (surface active agents) on the basis of their so-called hydrophile/lipophile balance (HLB). Unfortunately, as Becher and others are quick to point out, experiences with emulsions reported throughout the literature reveal that the HLB method has by no means obviated the need for trial and error.

The following U.S. patents by Benjamin R. Harris, taken in conjunction with the Becher text, cited supra (footnote 1), give further insight (practical) into the hydrophile/lipophile properties of emulsifying agents used to form W/O emulsions:

U.S. Pat. Nos. 2,109,842 issued Mar. 1, 1938; 2,114,490 issued Apr. 19, 1938; 2,177,983 issued Oct. 31, 1939; 2,294,233 issued Aug. 25, 1942.

The patents were uncovered in a recent study of the patent literature. In addition, the following patents were found:

| Patentee/s | Country | U.S. Pat. No. | Issued |
|---|---|---|---|
| Schanzle et al. | U.S. | 2,091,886 | 8-31-37 |
| Muller | U.S. | 2,350,800 | 6-6-44 |
| Nichols et al. | U.S. | 2,695,877 | 11-30-54 |
| Telle et al. | U.S. | 3,127,311 | 3-31-64 |
| Pader et al. | U.S. | 3,248,229 | 4-26-66 |
| Lachampt et al. | U.S. | 3,846,546 | 11-5-74 |
| Viout et al. | U.S. | 3,860,700 | 1-14-75 |
| Meguro et al. | U.S. | 3,875,196 | 4-1-75 |
| Lissant | U.S. | 3,892,881 | 7-1-75 |
| Thomas | U.S. | 3,929,499 | 12-30-75 |
| Johnson | G.B. | 417,715 | 10-1-34 |

Broadly speaking, careful study of each of these references shows that they are readily distinguishable from the present claimed discovery and they neither implicitly or explicitly suggest same. This will become even more apparent from the more detailed description hereinbelow of the claimed invention.

The transition from emulsion art to emulsion science, so to speak, is an arduous experience; it records and portends a path strewn with shattered predictions. Witness the oldest emulsions, viz, cosmetic emulsions, the preparation of which has traditionally been an art. Success has been consequent on trial and error and the judgment and good fortune of the "cosmeticulous." Only fairly recently, according to Becher, supra, can "... broad *generalizations* ... be made which will *guide* the uninitiated." (Emphasis added).[3]

[3] Ibid., page 245

It will be shown, infra, that the present discovery advances the art in a way which inherently flies in the teeth of present-day scientific, albeit somewhat eclectic, rationale. Typical of findings leading to this rationale are those reported in the periodical "Norda Schimmel," No. 430, pages 1–3, April 1971, published by Norda/Schimmel International, New York, N.Y. in which it is pointed out that:

"Emulsions of the water-in-oil type generally are not as stable as emulsions having water as the continuous phase. One reason is that the viscosity of the external phase changes with temperature." Page 1, col. 2.

It is further noted that when calcium stearate or aluminum stearate is used as the emulsifying agent it is best formed in situ. See page 1, column 1, and page 2 columns 1 and 2.

According to the periodical, also, calcium stearate is insoluble in water and mineral oil, "but ... sparingly soluble in mineral oil on heating." (Page 1, col. 1). Aluminum stearate, on the other hand, is "much more soluble in fatty oils and mineral oil" than calcium stearate:

"When 5 percent of aluminum stearate is stirred into mineral oil, the powder partially dissolves at room temperature, and on heating the solution becomes clear. At around 100° C the solution becomes highly viscous, behaving like a dispersion of a water-soluble gum in water. *On cooling, the solution sets to a gel which is not very stable.* Aluminum stearate is useful in W/O emulsions not only for its emulsifying activity but because it thickens or gels the oil phase. The high viscosity of the external phase helps to prevent coalescence of the water droplets and creaming of the emulsion." (Emphasis added) See paragraph bridging page 1, column 1 and page 2, column 1 of the periodical.

INVENTION

This invention relates to stable high internal phase ratio water-in-oil (W/O) emulsions. More particularly, the instant discovery concerns unique W/O emulsions containing predetermined concentrations of a phosphated mono- and/or di-glyceride and an aluminum or calcium stearate.

Cosmetically these emulsions are excellent as skin lotions and creams and they have superior stability. Quite surprisingly, they are prepared using emulsifiers which repel water and act normally as water barriers; in other words, these emulsifiers would not normally be expected to emulsify water in oil, much less form stable water-in-oil emulsions.

The skin lotions and creams prepared according to the present invention are characterized by their ability to form excellent barriers against outside moisture ($H_2O$), i.e., against penetration of outside moisture into the skin. Conversely, the W/O emulsions described herein effectively form a barrier against the escape of moisture i.e., through the skin and into the atmosphere, thus avoiding skin dryness. Other unique characteristics will be apparent from the more detailed description which follows.

According to the present invention water-in-oil type emulsion compositions having a continuous (external) oleaginous phase and a discontinuous (internal or disperse) aqueous phase are prepared having excellent stability at temperatures substantially above and below ambient (room) temperature for long periods of time. These compositions comprise, pursuant to the instant discovery, (a) a cosmetic emulsion oil, (b) an emulsifier combination comprising an aluminum and/or calcium stearate and a phosphated mono- and/or di-glyceride, and (c) water.

Conventional cosmetic emulsion oils are suitable for the present invention. Typical are the following:
mineral and/or other hydrocarbon oils, such as squalene, squalane, and the like;
fatty alcohol esters, such as stearyl alcohol esters of $C_{12}$ – $C_{18}$ fatty acids, isostearyl alcohol esters of $C_{12}$ – $C_{18}$ fatty acids, oleyl alcohol esters of $C_{12}$ – $C_{18}$ fatty acids;
waxes, such as beeswax, spermaceti, paraffin, petrolatum;
synthetic waxes, such as hydroxyethyl stearamide, cetyl stearate, stearic diethanolamide; and other like well-known cosmetic emulsion waxes.

Additional illustrations may be found throughout the art, e.g., cf. patents above cited.

The phosphated glyceride co-emulsifiers contemplated herein are well known. They are the alkali metal phosphoric acid ester salts of partial glycerides, i.e., the ester salts of mono- and di-glycerides.

The phosphated mono- and di-glycerides may be prepared in a number of ways. Generally, a derivative of phosphorus, such as phosphorus pentoxide, a polyphosphoric acid, or anhydrous phosphoric acid is reacted with the mono- or di-glyceride, or mixtures thereof, the fatty acid ester moiety or moieties of the glyceride being saturated and/or unsaturated (mono- or di-).

These and other methods of preparing the phosphated mono- and di-glycerides within the purview of the present invention are taught in the art. Illustrative literature is the following: U.S. Pat. Nos. 2,026,785, 2,177,983, 2,177,984, 3,248,229, and 3,875,196; British Pat. No. 1,174,789; Japanese Patent Publication No. 14322/68; German Pat. No. 719,830; Chem. Ber. 71, 1071 (1938); and Chem. Ber. 71, 1505 (1938).

In U.S. Pat. No. 3,875,196 for instance, phosphoric acid esters of mono- or di-glycerides are prepared by reacting a mono- or di-glyceride ester of stearic acid, myristic acid, palmitic acid, palmitoleic acid, or a mixed acid ester thereof, with a polyphosphoric acid. The polyphosphoric acid is prepared by heating phosphoric acid or by heat treating phosphoric acid with phosphorus pentoxide.

According to U.S. Pat. No. 3,875,196, the corresponding ester salts of the phosphated mono- and di-glycerides are prepared by neutralizing the glyceride ester. For example, glyceride ester crystals recovered from the reactions of a polyphosphoric acid and, say, a monoglyceride, are neutralized with an aqueous sodium hydroxide solution and the monosodium phosphoric acid ester of the monoglyceride is recovered.

In the present invention, the alkali metal phosphate salts of the glycerides are used as co-emulsifiers, sodium salt being preferred. However, one may employ mixtures of these phosphated monoglycerides, mixtures of the phosphated diglycerides, or mixtures of both. Of course, the fatty acid ester moieties in a diglyceride may be the same or different. For example, the fatty acid ester moieties of the diglyceride, such as those derived from $C_{12}$ – $C_{18}$ saturated, mono-unsaturated or di-unsaturated fatty acids, may be the same or different. Repeating, this co-emulsifier may be a blend of the various phosphated glycerides hereinabove mentioned.

The phosphated mono- and/or di-glyceride is present, according to the instant discovery, in the concentration of about 0.5 to about 5.0 percent by weight, preferably about 1.2 to about 3.75 percent, based upon the total weight of the emulsion composition.

As to the aluminum and/or calcium stearate, aluminum stearate is preferred. The concentration of said metal stearate/s employed in the emulsions of the present invention is in the range of about 0.5 to about 3.0 percent by weight, preferably about 1 to about 2.5 percent by weight, of the total weight of the emulsion.

It is a significant advantage of the instant discovery that up to about 85 percent water may be present as the disperse phase, based upon the total weight of the W/O emulsion. Generally from about 40 to about 85 percent water is present, preferably about 50 to about 78 percent.

As to the concentration of cosmetic emulsion oil in the compositions of the present invention, a quantity sufficient is added to provide the balance of components up to 100%.

Incorporation of conventional minor amounts of likewise conventional cosmetic emulsion additives is within the purview of the present invention. For example, up to about 0.3% by weight, based upon the total weight of the emulsion, of a preservative may be present in the claimed composition without modifying the basic nature of same. Similarly, fragrance and color can be added for aesthetic effects.

According to a preferred embodiment, the emulsifier combination and oil are pre-blended and water added thereto at an elevated temperature. It has been found that temperatures in the range of about 90° C to about 95° C are required, preferably using mild agitation over a period of a few minutes to an hour, or until the aluminum stearate, say, is adequately dispersed, to effect the high internal phase ratio water-in-oil emulsions of the present invention. More intense agitation may be employed, however, to produce the emulsions herein contemplated.

Skin lotions and creams prepared from the emulsions of the present discovery have exceptional shelf-life (stability) and, over extended periods of time and a very wide range of temperatures, resist breaking, flocculation and creaming. For example, stability for these extended periods is exhibited at temperatures as high as 45° C and as low as about −20° C.

Also, these lotions and creams when applied to the skin form a protective film thereon and stabilize moisture level by preventing excessive evaporation which causes skin dryness.

EXAMPLES

The present invention will better be understood from the following examples which are intended to be illustrative and not unduly limitative; unless otherwise indicated, percentages and parts recited in the examples are by weight:

EXAMPLE I

A moisturizing cream is prepared according to the present invention by adding 40.0 parts of water which has been heated to 92° C to the following mixture, which has been pre-heated to 92° C:

| Components | Parts |
| --- | --- |
| aluminum stearate | 3.0 |
| mineral oil | 8.5 |
| petrolatum | 17.0 |
| octadecyl isostearate | 10.0 |
| paraffin | 20.0 |
| phosphated glyceride | 1.5 |

The phosphated glyceride component is a mono-sodium phosphoric acid ester of a mono-glyceride of a mixture of oleic acid and linoleic acid (cottonseed oil fatty acids).

During the addition of water and subsequent thereto the mixture is stirred. Total stirring time period is about 30 minutes.

EXAMPLE II

A night cream is prepared by adding 68.0 parts of water which has been heated to 95° C to the following mixture, which has been preheated to 95° C.

| Components | Parts |
| --- | --- |
| aluminum stearate | 2.0 |
| mineral oil | 18.0 |
| petrolatum | 5.0 |
| octadecyl isostearate | 5.0 |
| phosphated glyceride | 2.0 |

The phosphated glyceride component is a mono-sodium phosphoric acid ester of a mono-glyceride of a mixture of oleic acid and stearic acid (partially-hydrogenated cottonseed oil fatty acids).

During the addition of water and subsequent thereto the mixture is stirred. Total stirring time period is about 60 minutes.

EXAMPLE III

A protective hand lotion is prepared by adding 83.5 parts of water which has been heated to 90° C to the following mixture, which has been preheated to 90° C:

| Components | Parts |
| --- | --- |
| aluminum stearate | 1.5 |
| mineral oil | 10.0 |
| petrolatum | 2.0 |
| phosphated glyceride | 3.0 |

The phosphated glyceride component is a mono-sodium phosphoric acid ester of a mono-glyceride of oleic acid (peanut oil fatty acid).

During the addition of water and subsequent thereto the mixture is stirred. Total stirring time period is about 60 minutes.

EXAMPLE IV

A barrier cream is prepared by adding 72.0 parts of water which has been heated to 90° C to the following mixture, which has been pre-heated to 90° C:

| Components | Parts |
| --- | --- |
| aluminum stearate | 3.0 |
| petrolatum | 7.0 |
| paraffin | 15.0 |
| phosphated glyceride | 3.0 |

The phosphated glyceride component is a mono-sodium phosphoric acid ester of a di-glyceride of a mixture of oleic acid and stearic acid (partially hydrogenated cottonseed oil fatty acids).

During the addition of water and subsequent thereto the mixture is stirred. Total stirring time period is about 30 minutes.

EXAMPLE V

A moisturizing lotion is prepared by adding 85.0 parts of water which has been heated to 94° C to the following mixture, which has been pre-heated to 94° C:

| Components | Parts |
| --- | --- |
| aluminum stearate | 0.5 |
| mineral oil | 5.0 |
| petrolatum | 4.5 |
| octadecyl isostearate | 2.0 |
| phosphated glyceride | 3.0 |

The phosphated glyceride component is a mono-sodium phosphoric acid ester of a di-glyceride of a mixture of oleic acid and linoleic acid (corn oil fatty acids).

During the addition of water and subsequent thereto the mixture is stirred. Total stirring time period is about 60 minutes.

EXAMPLE VI

A cleansing cream is prepared by adding 70.0 parts of water which has been heated to 92° C to the following mixture, which has been pre-heated to 92° C:

| Components | Parts |
| --- | --- |
| calcium stearate | 1.5 |
| mineral oil | 18.0 |
| petrolatum | 4.0 |
| paraffin | 3.5 |

| Components | Parts |
|---|---|
| phosphated glyceride | 3.0 |

The phosphated glyceride component is a mono-sodium phosphoric acid ester of di-glyceride of a mixture of oleic acid and linoleic acid (corn oil fatty acids).

During the addition of water and subsequent thereto the mixture is stirred. Total stirring time period is about 60 minutes.

Pursuant to statutory requirements, there are described above the invention and what are now considered its best embodiments. It should be understood, however, that the invention can be practiced otherwise than as specifically described, within the scope of the appended claims.

What is claimed is:

1. A high internal phase ratio cosmetic emulsion having a water disperse phase and an oil continuous phase which comprises (a) a cosmetic emulsion oil, (b) an emulsifier combination comprising aluminum and/or calcium stearate and an alkali metal phosphoric acid ester of a mono- and/or diglyceride, and (c) water, said components (a) (b) and (c) being present in the following concentration ranges expressed in percent by weight based upon the total weight of the resulting emulsion:

| Component | Concentration Range |
|---|---|
| (a) Cosmetic emulsion oil | balance |
| (b) Al/Ca stearate | 0.5 – 3.0 |
| Phosphated glyceride | 0.5 – 5.0 |
| (c) H$_2$O | 40.0 – 85.0 |

2. The emulsion of claim 1 wherein concentration ranges are:

| Component | Concentration Range |
|---|---|
| (a) Cosmetic emulsion oil | balance |
| (b) Al/Ca stearate | 1.0 – 2.5 |
| Phosphated glyceride | 1.2 – 3.75 |
| (c) H$_2$O | 50.0 – 78.0 |

3. The emulsion of claim 1 wherein the phosphated glyceride co-emulsifier is an alkali metal phosphoric acid ester of a monoglyceride.

4. The emulsion of claim 3 wherein the monoglyceride is the sodium phosphoric acid ester of the monoglyceride and the stearate is aluminum stearate.

5. The emulsion of claim 1 wherein the phosphated glyceride co-emulsifier is an alkali metal phosphoric acid ester of a diglyceride.

6. The emulsion of claim 5 wherein the diglyceride is the sodium phosphoric acid ester of the diglyceride and the stearate is aluminum stearate.

7. A method of preparing a high internal phase ratio cosmetic emulsion having a water disperse phase and an oil continuous phase which comprises (i) admixing (a) a cosmetic emulsion oil and (b) an emulsifier combination comprising aluminum and/or calcium stearate and an alkali metal phosphoric acid ester of a mono- and/or di-glyceride and (ii), while agitating, blending therewith (c) water which has been heated to a temperature in the range of about 90° to about 95° C, said components (a) (b) and (c) being present in the following concentration ranges expressed in percent by weight based upon the total weight of the resulting emulsion:

| Component | Concentration Range |
|---|---|
| (a) Cosmetic emulsion oil | balance |
| (b) Al/Ca stearate | 0.5 – 3.0 |
| Phosphated glyceride | 0.5 – 5.0 |
| (c) H$_2$O | 40.0 – 85.0 |

8. The method of claim 7 wherein the concentration ranges are:

| Component | Concentration Range |
|---|---|
| (a) Cosmetic emulsion oil | balance |
| (b) Al/Ca stearate | 1.0 – 2.5 |
| Phosphated glyceride | 1.2 – 3.75 |
| (c) H$_2$O | 50.0 – 78.0 |

9. The method of claim 7 wherein the phosphated glyceride co-emulsifier is an alkali metal phosphoric acid ester of a monoglyceride.

10. The method of claim 7 wherein the phosphated glyceride co-emulsifier is an alkali matal phosphoric acid ester of a diglyceride.

11. The method of claim 9 wherein the monoglyceride co-emulsifier is the sodium phosphoric acid ester of the monoglyceride and the stearate is aluminum stearate.

12. The method of claim 10 wherein the diglyceride co-emulsifier is the sodium phosphoric acid ester of the diglyceride and the stearate is aluminum stearate.

* * * * *